United States Patent
Puupponen et al.

(10) Patent No.: US 11,536,658 B2
(45) Date of Patent: Dec. 27, 2022

(54) METHOD FOR DETERMINING CONCENTRATION OF POLYELECTROLYTES AND PHOSPHONATES

(71) Applicant: Kemira Oyj, Helsinki (FI)

(72) Inventors: Salla Puupponen, Espoo (FI); Sari Krapu, Espoo (FI)

(73) Assignee: Kemira Oyj, Helsinki (FI)

( * ) Notice: Subject to any disclaimer, the term of this patent is extended or adjusted under 35 U.S.C. 154(b) by 0 days.

(21) Appl. No.: 17/281,827

(22) PCT Filed: Sep. 27, 2019

(86) PCT No.: PCT/FI2019/050695
§ 371 (c)(1),
(2) Date: Mar. 31, 2021

(87) PCT Pub. No.: WO2020/070386
PCT Pub. Date: Apr. 9, 2020

(65) Prior Publication Data
US 2022/0018774 A1      Jan. 20, 2022

(30) Foreign Application Priority Data

Oct. 1, 2018   (FI) .................................. 20185817

(51) Int. Cl.
*G01N 21/64* (2006.01)
*G01N 33/28* (2006.01)
*G01N 21/77* (2006.01)

(52) U.S. Cl.
CPC ....... *G01N 21/6408* (2013.01); *G01N 21/643* (2013.01); *G01N 33/2823* (2013.01); *G01N 2021/7786* (2013.01)

(58) Field of Classification Search
CPC ............. G01N 21/6408; G01N 21/643; G01N 33/2823; G01N 2021/7786; G01N 21/77; G01N 31/22
See application file for complete search history.

(56) References Cited

U.S. PATENT DOCUMENTS 7,524,630 B2 *   4/2009   Tan .................. G01N 33/54393
                                                          436/526
9,194,802 B2 *  11/2015   Pierre .................. G01N 33/542
(Continued)

FOREIGN PATENT DOCUMENTS

EP      1666560 A1    6/2006
EP      1499895 B1    5/2008
(Continued)

OTHER PUBLICATIONS

International Search Report and Written Opinion for International Application No. PCT/FI2019/050695 dated Dec. 19, 2019.
(Continued)

*Primary Examiner* — David P Porta
*Assistant Examiner* — Djura Malevic
(74) *Attorney, Agent, or Firm* — Meunier Carlin & Curfman LLC

(57) ABSTRACT

The present invention provides a method for determining concentration of polyelectrolyte or phosphonate in a sample comprising polyelectrolyte or phosphonate in low concentrations. The method comprises admixing the sample with a reagent comprising a lanthanid(lll) ion; admixing the sample with silica; allowing the polyelectrolyte or phosphonate in the sample to interact with the reagent comprising the lanthanide(lll) ion and the silica; exciting the sample and detecting a sample signal deriving from the lanthanide(lll) ion by time-resolved fluorescence measurement; and deter-
(Continued)

mining the concentration of the polyelectrolyte or phosphonate in the sample by using the detected sample signal.

20 Claims, 1 Drawing Sheet

(56) References Cited

U.S. PATENT DOCUMENTS

| | | | | |
|---|---|---|---|---|
| 2004/0067503 | A1* | 4/2004 | Tan | B82Y 15/00 436/526 |
| 2006/0141486 | A1 | 6/2006 | Coonan et al. | |
| 2014/0080163 | A1* | 3/2014 | Pierre | G01N 33/542 436/98 |
| 2020/0132602 | A1 | 4/2020 | Favero et al. | |
| 2022/0018774 | A1* | 1/2022 | Puupponen | G01N 21/6408 |

FOREIGN PATENT DOCUMENTS

| | | |
|---|---|---|
| FR | 3064364 A1 | 9/2018 |
| WO | 9216840 A1 | 10/1992 |
| WO | 0061282 A1 | 10/2000 |
| WO | 2015075299 A1 | 5/2015 |
| WO | 2015075308 A1 | 5/2015 |
| WO | 2016066885 A1 | 5/2016 |

OTHER PUBLICATIONS

Inna V Melnyk et al., "Dy(III) sorption from water solutions by mesoporous silicas functionalized with phosphonic acid groups", Journal of Porous Materials, Kluwer Academic Publishers, Bo, vol. 19, No. 5, Aug. 23, 2011, pp. 579-585.

Search Report for Finnish Application No. 20185817 dated May 23, 2019.

* cited by examiner

METHOD FOR DETERMINING CONCENTRATION OF POLYELECTROLYTES AND PHOSPHONATES

PRIORITY

This is a U.S. national application of the international application number PCT/FI2019/050695 filed on Sep. 27, 2019, and claiming priority of FI 20185817 filed on Oct. 1, 2018, the contents of both of which are incorporated herein by reference.

FIELD OF THE INVENTION

The present invention relates to a method for determining concentration of polyelectrolytes or phosphonates in a sample with time resolved fluorescence.

BACK GROUND

Quantification of organic polymers is essential in many fields of industry such as in water treatment, paper and oil industries. The organic polymers desired to be analyzed may be corrosion inhibitors, antiscalants or enhanced oil recovery (EOR).

Several quantification and analysis methods of organic polymers have been developed, such as time-resolved luminescence measurement.

By utilizing lanthanide(III) time-resolved luminescence measurement organic polymers can be measured in a rapid, easy and often affordable manner Organic polymers containing two or more chelating groups often increase the time resolved luminescence intensity of lanthanide(III) ions. These chelating groups may be e.g. carboxylates, sulfonates, carboxamides, phosphates, phosphonates or amines.

The time resolved fluorescence (TRF) signal amplification is dependent on the polymer concentration and can be thus utilized in quantification of the polymeric samples.

Often, the TRF detection limit of organic polymers is too low for practical use. For instance, water treatment plants use often very low concentrations of antiscalants and corrosion inhibitors.

The scale inhibitors may be detected by admixing the lanthanide(III) ion with the organic polymer analyte, after which the signal of the lanthanide-polymer chelate is measured by time-gated luminescence. However, the simple admixing of the polymer with the lanthanide(III) does not always amplify the TRF signal sufficiently for quantification of low concentrations.

Therefore, there is a need for a method for determining concentration of polyelectrolytes or phosphonates in a sample comprising organic polymers in low concentrations.

SUMMARY OF THE INVENTION

An object of the present invention is to provide a method for determining concentration of polyelectrolytes or phosphonates in a sample comprising low amounts of polyelectrolytes or phosphonates.

Another object of the present invention is to provide a simple and efficient method for determining concentration of polyelectrolytes or phosphonates in a sample comprising low amounts of polyelectrolytes or phosphonates.

The inventors surprisingly found that TRF signal of polyelectrolyte or phosphonate chelated lanthanide(III) can be amplified with addition of small size molecules capable of chelating.

It was surprisingly found that addition of small amount of soluble silica such as silicic acid, sodium silicate, oligomeric silica, or a mixture thereof was observed to amplify the TRF signal of lanthanide(III)-polyelectrolyte or -phosphonate chelates. Silica alone increases only slightly the lanthanide (III) TRF signal, but the amplification is much greater when the polyelectrolyte or phosphonate is added into the solution.

Without bounding to any theory, the signal amplification may be due to the more optimal configuration of the lanthanide(III)-polymer-silica chelate (less folding of the analyte), possible changes in the coordination number of the chelated lanthanide(III) (high coordination numbers are favored) and more efficient protection of lanthanide(III) from water (water molecules quench the TRF signal by radiationless decay process).

In the present invention the silica additive is used to sensitize the TRF signal of lanthanide(III)-organic polymer; to detect lower concentrations of the analyte. The cooperation of the additive and organic polymer can also be used for research of the analyte properties.

With the method of the present invention low concentrations of polyelectrolytes or phosphonates in a sample can be detected.

DETAILED DESCRIPTION

Figure 1:
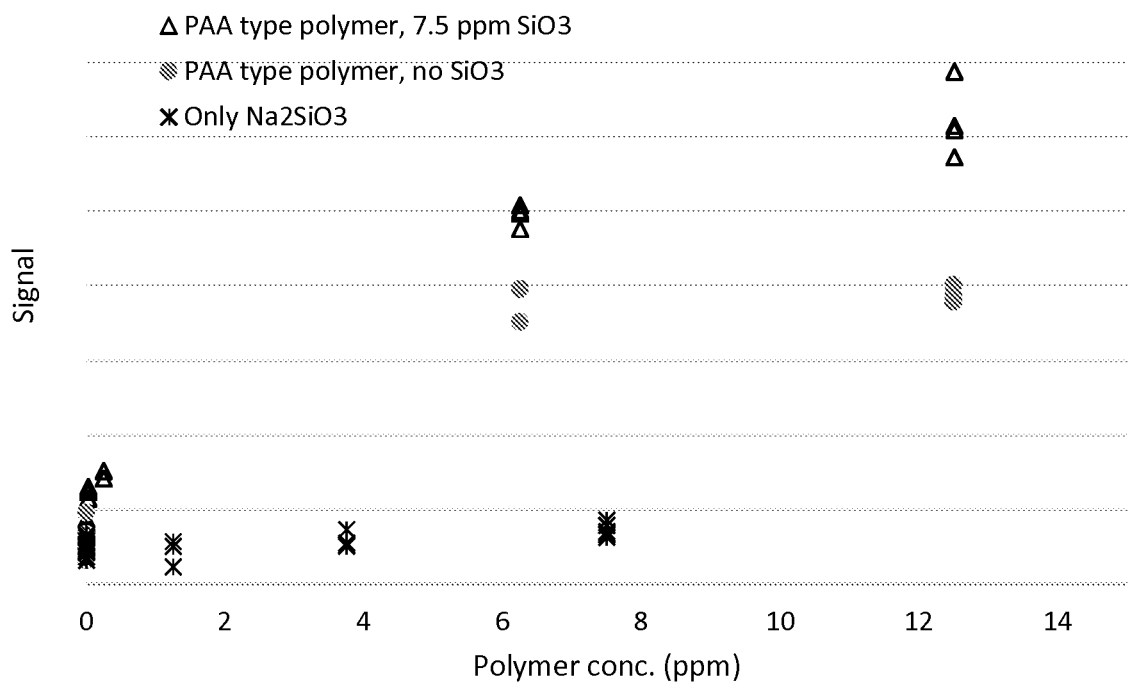
FIG. 1 illustrates TRF signal of lanthanide(III)-polymer chelates as a function of polymer concentration, with and without Na2SiO3.

The present invention relates to a method for determining concentration of organic polyelectrolytes or phosphonates in a sample comprising organic polymers. More particularly the present invention relates to a method for determining concentration of polyelectrolytes or phosphonates in a sample comprising organic polymers, the method comprising optionally diluting and/or purifying the sample,
admixing the sample with a reagent comprising a lanthanide(III) ion,
admixing the sample with silica,
allowing the polyelectrolyte or phosphonate in the sample to interact with the reagent comprising the lanthanide (III) ion and the silica,
exciting the sample at a excitation wavelength and detecting a sample signal deriving from the lanthanide(III) ion at a signal wavelength by using time-resolved fluorescence measurement, and
determining the concentration of the polyelectrolyte or phosphonate in the sample by using the detected sample signal.

The analyte, polyelectrolyte or phosphonate, in the sample bears one or more groups that can hydrolyze and/or that the sample bears one or more groups that are capable of dissociating in aqueous solution to form either anion or cation groups. The analyte can be zwitterionic, i.e. contain both cationic and anionic groups. The charging of the group can depend on the environment pH (acidic or basic groups, such as carboxylic acids and amino groups). Therefore, the groups capable for dissociation can be neutral in certain pH (e.g. carboxylic acid group in acidic and amino groups in basic environment). The polyelectrolyte can be basic or acidic.

The polyelectrolyte contains two or more groups capable of chelating with the lanthanide(III) ion. Preferably these groups are selected from esters, ethers, hydroxyls, thiols, carboxylates, sulfonates, amides, phosphates, phosphonates, amine groups or a mixture thereof.

The polyelectrolyte may contain only one of the groups, or at least two of the groups. The organic polymer may be homopolymer or copolymer.

In one embodiment the polyelectrolyte is protein or oligopeptide.

Examples of the polyelectrolyte is polyacrylic acid, maleic acid, sodium allyl sulfonate, polyacrylamide, polyamine such as polyethyleneimine and polydiallyldimethylammonium chloride or any co- or terpolymer of these polymers.

In one embodiment the polyelectrolyte has molecular weight of at least 1000 g/mol.

In another embodiment the phosphonate has molecular weight of at least 100 g/mol.

In one embodiment concentration of phosphonic acid containing two or more groups capable of chelating with the lanthanide(III) is determined. Preferably the phosphonic acid is hydroxyethylidene diphosphonic acid, aminotris(methylenephosphonic acid), ethylenediamine tetra(methylene phosphonic acid), diethylenetriamine penta(methylene phosphonic acid).

With the method of the present invention polyelectrolytes, phosphates and phosphonic acid in low concentrations in a sample can be detected.

In one embodiment concentration of the polyelectrolyte or phosphonate in the measurement mixture is in the range of 0.01-500 ppm, preferably 0.5-50 ppm, and more preferably 0.5-20 ppm.

In case the concentration of the polyelectrolyte or phosphonate r in the sample is higher, the sample can be diluted.

In another embodiment concentration of the silica in the measurement mixture is in the range of 0.05-200 ppm, preferably 0.5-100 ppm, and more preferably 0.5-50 ppm.

The silica can be any soluble silicate except salts that may interfere with the measurement, such as trivalent cations. Examples of suitable silica are silicic acid, silicates, oligomeric silica or a mixture thereof.

In one embodiment concentration of the lanthanide(III) ion in the measurement mixture is in the range of 0.1-100 $\mu$M, preferably 0.1-50 $\mu$M, and more preferably 1-20 $\mu$M.

By term "measurement mixture" is meant the admixture in the measurement.

The lanthanide(III) ion is selected from europium, terbium, samarium or dysprosium ions, preferably europium or terbium ions.

The concentrations of the polyelectrolyte or phosphonate, silica and the lanthanide(III) ion refer to concentrations present in the measurement.

In a preferred embodiment the lanthanide(III) ion is a lanthanide(III) salt or luminescent lanthanide chelate. The lanthanide(III) salt is selected from halogenides and oxyanions, such as nitrates, sulfates or carbonates, preferably from hydrated halogenides or nitrates, more preferably chloride.

In one embodiment a signal modifier is added to the sample before the excitation of the sample. The signal modifier comprises a metal ion selected from a group comprising copper, nickel, chromium, iron, gold, silver, cobalt, and any of their mixtures.

The sample may be optionally diluted or purified prior mixing the sample with the reagent comprising a lanthanide (III) ion.

The sample is optionally purified by using a purification method selected from centrifugation, size exclusion chromatography, cleaning with solid-phase extraction (SPE) cartridges, dialysis techniques, extraction methods for removing hydrocarbons, filtration, microfiltration, ultrafiltration, nanofiltration, membrane centrifugation and any combinations thereof. It should be understood that the purification treatment step means preferably removal or dilution of molecules that may disturb the examination of charged molecules of interest, not isolation of the polyelectrolyte e.g. by chromatography.

The polyelectrolyte or phosphonate is optionally diluted to suitable aqueous solution e.g. deionized water or brine containing monovalent and/or divalent ions. Preferably, the dissolution brine does not contain any trivalent ions. If the polymer solution contains some interfering compounds, suitable pretreatment procedures may be applied prior to the dilution steps. Preferably the sample is an aqueous solution.

In one embodiment pH value of the sample is adjusted to a level in range between pH 3 and pH 8, preferably in range from pH 5 to pH 7.5.

In one embodiment the sample is admixed with the silica prior admixing the sample with the reagent comprising a lanthanide(III) ion.

In another embodiment the sample is admixed with the reagent comprising a lanthanide(III) ion prior admixing the sample with the silica.

In another embodiment the reagent comprising a lanthanide(III) ion and the silica is admixed with the sample at the same time.

In a preferred embodiment buffer is used in the measurement for standardization of the pH. Preferably, the buffer is non-chelating, zwitterionic Good's buffer, such as HEPES or tris-bis propane. The pH of the buffer solution is adjusted to a suitable range, preferably to pH 5-7.5. The pH should not be excessively alkaline in order to prevent possible precipitation of the lanthanide hydroxides.

Unknown concentration of the polyelectrolyte or phosphonate in the sample is determined by comparing the sample signal to calibration curve. The calibration curve is obtained from TRF measurement of calibration standard samples with varying polyelectrolyte or phosphonate concentrations. Same dilution and or purification steps and measurement parameters have to be used for both the sample and calibration samples.

The lanthanide(III) ion is excited at excitation wavelength and measured at emission wavelength and detected by using time-resolved fluorescence (TRF). Any TRF reader can be employed. Excitation and emission wavelengths are selected so that the S/N is the best. Also the delay time can be optimized.

The excitation and emission wavelengths and the delay time are chosen based on the requirements of the lanthanide ion.

In an exemplary embodiment excitation wavelength and emission wavelength and delay time for Europium is 395 nm and 615 nm and 400 µs respectively.

The present invention further relates to use of the method of the present invention for determining concentration of polyelectrolyte or phosphonate in a sample.

The sample can originate from an oilfield, an oil well, an oil production process, paper manufacturing process, mining industry or water treatment process such as desalination, drinking water or wastewater treatment processes.

The present invention further relates a device comprising means for performing the method according to the present invention for determining concentration of polyelectrolyte or phosphonate in a sample.

The examples are not intended to limit the scope of the invention but to present embodiments of the present invention.

EXAMPLES

All the reagents were diluted into brine, which composition is presented in Table 1. $EuCl_3.6H_2O$ was used as lanthanide source and sodium silicate ($Na_2SiO_3$) as TRF signal enhancer. The europium salt and $Na_2SiO_3$ were diluted into the brine so that the concentrations of europium and $Na_2SiO_3$ were 11.24 μM and 7.5 ppm, respectively, in the measurement solution. Fresh and dilute silica solution was used in order to prevent excess polymerization of the silica species. The polymer concentration was varied between 0 and 25 ppm in the measurement mixture. Analytes tested were polyacrylic acid and sodium allyl sulphonate maleic acid copolymer type polymers. 100 μl of lanthanide solution was first pipetted into microplate (MICROPLATE BIOCHEM 96WELL BLACK), after which 50 μl of silica solution and 50 μl of polymer solution were added to the plate. The TRF signal of the mixture was measured using Tecan Spark multiplate reader. The lag time, excitation and emission wavelengths used were 400 μs, 295 nm and 615 nm, respectively.

FIG. 1 presents time resolved fluorescence signals of lanthanide(III)-polyacrylic acid (PAA) type polymer, lanthanide(III)-$Na_2SiO_3$ and lanthanide(III)-PAA+$Na_2SiO_3$.

Figure 2:
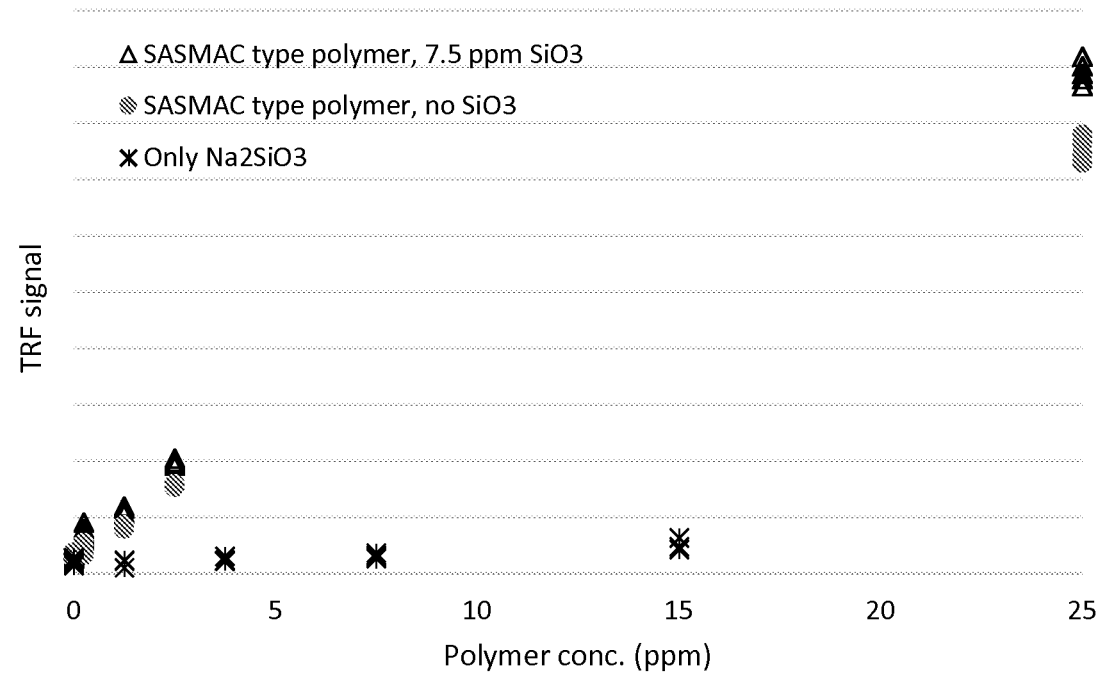
FIG. 2 illustrates TRF signal of lanthanide(III)-polymer chelates as a function of polymer concentration with Na2SiO3 and Na2SiO3 alone.

FIG. 2 presents time resolved fluorescence signals of lanthanide(III)-sodium allyl sulphonate maleic acid copolymer (SASMAC), lanthanide(III)-$Na_2SiO_3$ and lanthanide(III)-SASMAC+$Na_2SiO_3$.

TABLE 1

Brine composition used in tests. The salts are dissolved into 10.00 kg of MQ water.

| Salt | Mass (g) |
| --- | --- |
| NaCl | 350.3 |
| $CaCl_2*2H_2O$ | 22.4 |
| $MgCl2*6H_2O$ | 14.6 |
| KCl | 2.1 |
| $BaCl_2*2H_2O$ | 1.3 |

The invention claimed is:

1. A method for determining concentration of polyelectrolyte or phosphonate in a sample comprising polyelectrolyte or phosphonate, the method comprising:
   optionally diluting and/or purifying the sample;
   admixing the sample with a reagent comprising a lanthanide(lll) ion;
   admixing the sample with silica;
   allowing the polyelectrolyte or phosphonate in the sample to interact with the reagent comprising the lanthanide (lll) ion and the silica;
   exciting the sample at a excitation wavelength and detecting a sample signal deriving from the lanthanide(lll) ion at a signal wavelength by using time-resolved fluorescence measurement; and
   determining the concentration of the polyelectrolyte or phosphonate in the sample by using the detected sample signal.

2. The method according to claim 1, wherein concentration of the polyelectrolyte or phosphonate in the measurement mixture is in the range of 0.01500 ppm.

3. The method according to claim 2, wherein concentration of the polyelectrolyte or phosphonate in the measurement mixture is in the range of 0.5-50 ppm.

4. The method according to claim 1, wherein concentration of the silica in the measurement mixture is in the range of 0.05-200 ppm.

5. The method according to claim 4, wherein concentration of the silica in the measurement mixture is in the range of 0.5-100 ppm.

6. The method according to claim 4, wherein concentration of the lanthanide(III) ion in the measurement mixture is in the range of 0.1-50 μM.

7. The method according to claim 1, wherein concentration of the lanthanide(lll) ion in the measurement mixture is in the range of 0.1-100 μM.

8. The method according to claim 1, wherein the silica comprises silicic acid, silicates, oligomeric silica or a mixture thereof.

9. The method according to claim 1, wherein the polyelectrolyte or phosphonate contains two or more groups capable of chelating with the lanthanide(III) ion, preferably selected from esters, ethers, hydroxyls, thiols, carboxylates, sulfonates, amides, phosphates, phosphonates and/or amine groups.

10. The method according to claim 1, wherein concentration of phosphonic acid containing two or more groups capable of chelating with the lanthanide(III) is determined.

11. The method according to claim 10, wherein the phosphonic acid is selected from hydroxyethylidene diphosphonic acid, aminotris(methylenephosphonic acid), ethylenediamine tetra(methylene phosphonic acid), and diethylenetriamine penta(methylene phosphonic acid).

12. The method according to claim 1, wherein the lanthanide(lll) ion is selected from europium, terbium, samarium or dysprosium ions, preferably europium or terbium ions.

13. The method according to claim 1, wherein a signal modifier is added to the sample before the excitation of the sample.

14. The method according to claim 13, wherein the signal modifier comprises a metal ion selected from the group comprising copper, nickel, chromium, iron, gold, silver, cobalt, and any of their mixtures.

15. The method according to claim 1, wherein the sample is purified by using a purification method selected from the group consisting of centrifugation, size exclusion chromatography, cleaning with solid-phase extraction (SPE) cartridges, dialysis techniques, extraction methods for removing hydrocarbons, filtration, microfiltration, ultrafiltration, nanofiltration, membrane centrifugation and any combinations thereof.

16. The method according to claim 1, wherein a pH value of the sample is adjusted to a level in a range between pH 3 and pH 8.

17. The method according to claim 1, wherein the sample is admixed with the silica prior admixing the sample with the reagent comprising a lanthanide(III) ion; or the sample is admixed with the reagent comprising a lanthanide(III) ion prior admixing the sample with the silica; or the sample is admixed with the reagent comprising a lanthanide(III) ion and the silica at the same time.

18. The method according to claim 1, wherein the sample originates from an oilfield, an oil well, an oil production process, paper manufacturing process, mining industry or water treatment process.

19. The device comprising means for performing the method according to claim 1 for determining concentration of polyelectrolyte or phosphonate in a sample.

20. The method according to claim 1, wherein the reagent comprising a lanthanide(III) ion is a lanthanide(III) salt or a luminescent lanthanide chelate.

\* \* \* \* \*